United States Patent
Attolino et al.

(10) Patent No.: US 11,180,454 B2
(45) Date of Patent: Nov. 23, 2021

(54) SYNTHESIS OF AN AZASUGAR AND INTERMEDIATES THEREOF

(71) Applicant: DIPHARMA SA, Chiasso (CH)

(72) Inventors: Emanuele Attolino, Baranzate (IT); Niccolo Santillo, Baranzate (IT); Gabriele Razzetti, Baranzate (IT)

(73) Assignee: DIPHARMA SA, Chiasso (CH)

( * ) Notice: Subject to any disclaimer, the term of this patent is extended or adjusted under 35 U.S.C. 154(b) by 63 days.

(21) Appl. No.: 16/628,442

(22) PCT Filed: Jul. 10, 2018

(86) PCT No.: PCT/EP2018/068648
§ 371 (c)(1),
(2) Date: Jan. 3, 2020

(87) PCT Pub. No.: WO2019/020362
PCT Pub. Date: Jan. 31, 2019

(65) Prior Publication Data
US 2020/0216393 A1    Jul. 9, 2020

(30) Foreign Application Priority Data
Jul. 11, 2017 (IT) .......................... 102017000078102

(51) Int. Cl.
*C07D 211/46* (2006.01)
*C07D 211/02* (2006.01)

(52) U.S. Cl.
CPC .......... *C07D 211/46* (2013.01); *C07D 211/02* (2013.01)

(58) Field of Classification Search
CPC ........................... C07D 211/02; C07D 211/46
See application file for complete search history.

(56) References Cited

FOREIGN PATENT DOCUMENTS

| EP | 3081555 | * | 10/2016 |
| EP | 3081555 A1 | | 10/2016 |
| WO | 2008/045015 | * | 4/2008 |
| WO | 045015 A1 | | 4/2008 |

OTHER PUBLICATIONS

Reddy, Chem & Biol Interface, vol. 2 (4), 2012, 251-257. (Year: 2012).*
International Search Report dated Nov. 19, 2018 for PCT/EP2018/068648.

* cited by examiner

*Primary Examiner* — D Margaret M Seaman
(74) *Attorney, Agent, or Firm* — Lucas & Mercanti, LLP

(57) ABSTRACT

The present invention relates to a process for the preparation of migalastat of formula (I) and intermediates useful in the synthesis thereof. The process comprises the double reductive amination reaction of a compound of formula (VI).

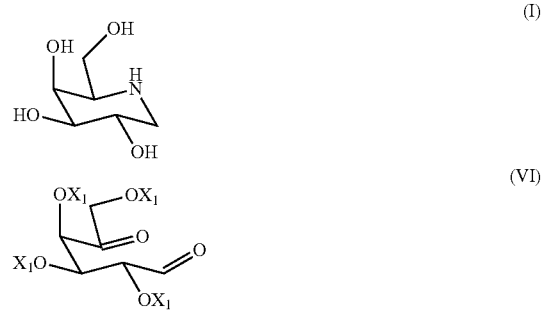

16 Claims, 1 Drawing Sheet

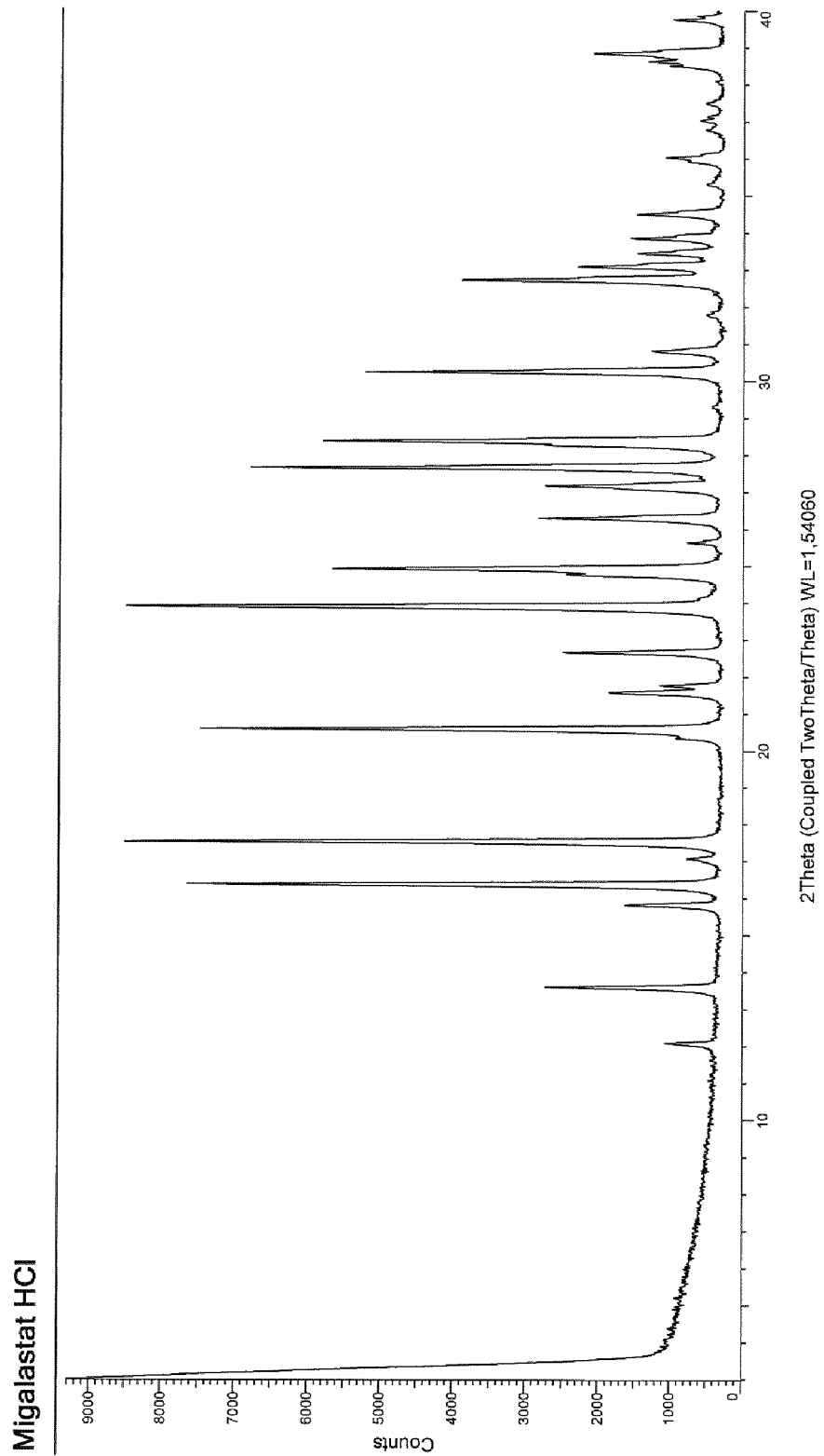

SYNTHESIS OF AN AZASUGAR AND INTERMEDIATES THEREOF

The present invention relates to a process for the preparation of intermediates useful in the synthesis of the galactosidase inhibitor migalastat.

BACKGROUND OF THE INVENTION (2R,3S,4R,5S)-2-(Hydroxymethyl)-3,4,5-trihydroxypiperidine of formula (I),

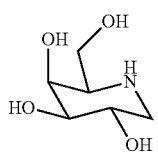

(I)

also known as 1,5-dideoxy-1,5-imino-D-galactitol, 1-deoxygalactonojirimycin (DGJ) or migalastat, is a potent inhibitor of the alpha and beta-galactosidases, which are important enzymes for the metabolism of complex carbohydrates. Inhibitors of said enzymes have been studied in the treatment of various diseases, including diabetes (U.S. Pat. No. 4,634,765), cancer (U.S. Pat. No. 5,250,545), herpes (U.S. Pat. No. 4,957,926), HIV or Fabry Disease (Fan, J. Q. et al. *Nat. Med.* 1999, 5, 112).

Migalastat is a representative of iminosugars or azasugars, a family of polyhydroxylated heterocycles comprising one endocyclic nitrogen atom. The first synthesis of these compounds was reported in the early 1960s (Paulsen, H., *Angew. Chem. Int. Ed. Engl.* 1962, 1, 454; Jones, J. K. N. et al., *Can. J. Chem.* 1963, 41, 636; Hanessian, S. et al., *J. Org. Chem.* 1963, 28, 2604). In 1966, Inuoye et al. isolated for the first time nojirimycin of formula (II) from strains of *Streptomyces* (Inuoye et al. *J. Antibiot.* 1966, 9, 288), in the following year Paulsen et al. reported the first synthesis of 1-deoxynojirimycin of formula (III) (Paulsen et al. *Chem. Ber.* 1967, 100, 802).

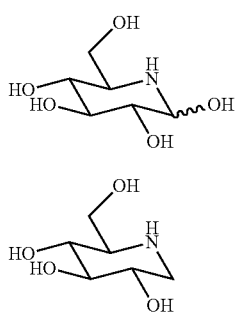

(II)

(III)

Since then, the interest in iminosugars has increased thanks to the discovery of their potent inhibitory activity of glycosidases. At physiological pH value, the nitrogen atom is positively charged and this allows an interaction with the terminal carboxylates present in the active site of the enzyme. In addition, iminosugars are structurally similar to the oxygen analogues present in nature.

However, 1-deoxygalactonojirimycin is not present in nature and has thus to be prepared. The first synthetic route was disclosed by Paulsen et al. (*Chem. Ber.* 1980, 113, 2601) starting from 1,6-anhydro-α-D-galactofuranose. Since then, various synthetic procedures to 1-deoxygalactonojirimycin have been published using as starting materials sugars or analogues of sugars.

An interesting approach for the synthesis of galacto-configurated azasugars has been reported by Barili et al. (*Tetrahedron* 1997, 53, 3407). The authors describe the preparation of 1-deoxy galactonojirimycin by double reductive amination starting from L-arabino-hexos-5-ulose of formula (IVa) (Scheme 1) with benzhydrylamine and a subsequent debenzylation step. The yield in the key reaction step of double reductive amination was found to be 36%.

Scheme 1

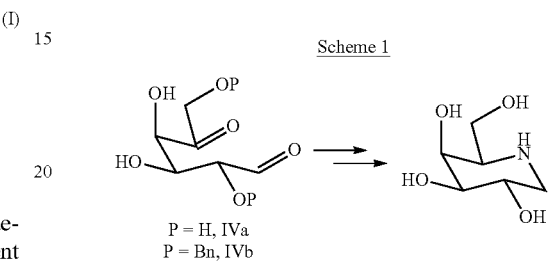

P = H, IVa
P = Bn, IVb

The so obtained D-galacto-isomer was then purified by chromatography. Also in the case of the di-protected derivative of formula (IVb) with different amines, the final product had to be purified by chromatography. Moreover, the reported procedure makes use of $NaCNBH_3$ as reducing agent, which is used in excess with respect to compound of formula (IV), in specific 2.2 moles of reducing agent per mole of L-arabino-hexos-5-ulose of formula (IVa). Important precautions have to be taken when using $NaCNBH_3$ in order to prevent the release of toxic and dangerous HCN. Furthermore, the article does not mention how to dispose the wastewater containing cyanide ions, which is a major issue in order to make the process applicable at an industrial scale.

Therefore, there is a need for a new method for the preparation of migalastat of formula (I), which overcomes the disadvantages mentioned above and which allows to obtain the desired product in an efficient manner on an industrial scale, safe for human health and the environment and in high yield and purity, in particular stereochemical purity.

BRIEF DESCRIPTION OF THE FIGURE AND ANALYTICAL METHODS

Migalastat HCl in crystalline form, herein referred to as form I, was characterized by X-ray powder diffraction (XRPD). The XRPD spectra were collected with the automatic powder and liquid diffractometer Bruker D8 Advance with a PSD LynxEye detector at the following operating conditions: Bragg-Brentano geometry, Cu Kd (λ=1.54 Å) radiation filtered with Nickel and scanning from 3 to 40° degrees with 2θ and an angular step time of 0.02° in 1 sec.

FIG. 1 shows the XRPD spectrum of migalastat HCl in crystalline form, herein referred to as form I, characterized by an XRPD pattern having peaks at (expressed in ° in 2θ): 12.07; 13.58; 15.81; 16.37; 17.06; 17.53; 20.59; 21.59; 21.75; 22.67; 39.95; 24.92; 26.30; 27.16; 27.67; 28.37; 30.26; 30.81; 32.74; 33.11; 33.46, 33.87 and 34.52±0.2° in 2θ.

SUMMARY OF THE INVENTION

The object of the present invention is a process for the preparation of a compound of formula (V) or a salt thereof

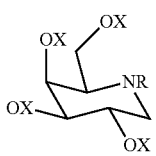

(V)

wherein X, equal to each other, is hydrogen or an alcohol protecting group,
R is hydrogen, $C_1$-$C_6$ alkyl, or an amino protecting group;
comprising the double reductive amination step of a dicarbonyl compound of formula (VI)

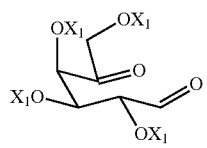

(VI)

wherein each of $X_1$, equal to each other, is an alcohol protecting group, with an amine $NH_2$—R or a salt thereof
in the presence of a reducing agent and a solvent and, if the case,
the conversion of a compound of formula (V) into another compound of formula (V) or a salt thereof, and/or the conversion of a salt of a compound of formula (V) into its free base.

DETAILED DESCRIPTION OF THE INVENTION

The object of the present invention is a process for the preparation of a compound of formula (V) or a salt thereof

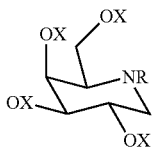

(V)

wherein X, equal to each other, is hydrogen or an alcohol protecting group,
R is hydrogen, $C_1$-$C_6$ alkyl, or an amino protecting group;
comprising the double reductive amination step of a dicarbonyl compound of formula (VI)

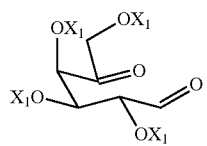

(VI)

wherein each of $X_1$, equal to each other, is an alcohol protecting group, with an amine of formula (VII) or a salt thereof

 (VII)

wherein R is as defined above,
in the presence of a reducing agent and a solvent and, if the case, the conversion of a compound of formula (V) into another compound of formula (V) or a salt thereof, and/or the conversion of a salt of a compound of formula (V) into its free base, and, if the case,
the separation of a single isomer from a mixture thereof.

The alcohol-protecting group X and $X_1$ are for example a protecting group known from carbohydrate chemistry, for example, benzyl, allyl, acetyl or benzoyl group.

A preferred alcohol-protecting group is benzyl.

A $C_1$-$C_6$ alkyl group, which may be linear or branched, is typically a $C_1$-$C_4$ alkyl group, such as methyl, ethyl, propyl, isopropyl or butyl, isobutyl, tert-butyl. The $C_1$-$C_6$ alkyl group may be optionally substituted by one or more substituents, which may be the same or different, preferably from one to three substituents such as hydroxy or halogen, in particular chlorine or fluorine.

The amino protecting group is for example a protecting group known from the chemistry of peptides, for example benzyl, benzhydryl, triphenylmethyl, 1-phenylethyl, benzyloxycarbonyl and tert-butoxycarbonyl, preferably benzyl, benzhydryl, triphenylmethyl or 1-phenylethyl.

In an amine of formula (VII), or a salt thereof, R is preferably benzyl, benzhydryl, triphenylmethyl or 1-phenylethyl. In the case of 1-phenylethyl, the amine of formula (VII) can be optically active with the absolute configuration (S) ((1S)-1-phenylethylamine or (S)-PhEA) or (R) ((1R)-1-phenylethylamine or (R)-PhEA), or a stereoisomeric mixture thereof.

A preferred amino protecting group is benzyl.

A further preferred amino protecting group is benzhydryl.

A further preferred amino protecting group is triphenylmethyl.

A further preferred amino protecting group is 1-phenylethyl, wherein the corresponding amine has the absolute configuration (S) or (R) or a stereoisomeric mixture thereof.

A further preferred amino protecting group is 1-phenylethyl, wherein the corresponding amine has the absolute configuration (S).

A further preferred amino protecting group is 1-phenylethyl, wherein the corresponding amine has the absolute configuration (R).

The reducing agent used in the reductive amination reaction can be for example $NaCNBH_3$.

In a further embodiment, the reducing agent used in the reductive amination reaction can be for example $NaBH_4$.

In an additional embodiment, the reducing agent used in the reductive amination reaction can be for example $NaBH(OAc)_3$.

In yet a further embodiment, the reducing agent used in the reductive amination reaction can be for example a borane complex with an amine of formula (VIII)

 (VIII), wherein each of the substituents Y, being the same or different, is hydrogen, an optionally substituted $C_1$-$C_6$ alkyl or aryl group, or two of Y, taken together with the nitrogen atom to which they are linked, form a $C_5$-$C_6$ heterocyclyl ring optionally containing an oxygen atom or a NRa group, wherein Ra is hydrogen, an amino-protecting group, or a $C_1$-$C_4$ alkyl group.

In yet a further embodiment, the reducing agent used in the reductive amination reaction can be for example a borane complex with a pyridine of formula (IX)

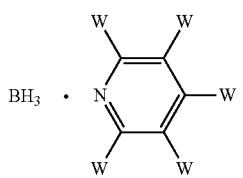

wherein each of the W substituents, which are the same or different, is hydrogen, an optionally substituted $C_1$-$C_6$ alkyl, or a halogen atom.

A preferred amine of formula (VIII) is piperidine.

A further preferred amine of formula (VIII) is morpholine.

A further preferred amine of formula (VIII), wherein the $C_5$-$C_6$ heterocyclyl ring contains a NRa group, is piperazine, wherein Ra is hydrogen or a $C_1$-$C_4$ alkyl group, and wherein the $C_1$-$C_4$ alkyl group is preferably methyl, ethyl or propyl.

An aryl group can be for example phenyl. The phenyl can be optionally substituted by one to three substituents, which may be the same or different, selected independently from a linear or branched $C_1$-$C_4$ alkyl group, which in its turn can be optionally substituted by one to three halogen atoms, typically fluorine; a hydroxy group; a $C_1$-$C_4$ alkoxy group, for example methoxy; a halogen atom, such as bromine or chlorine; a cyano group; and a nitro group.

The reducing agents of formula (VIII) or of formula (IX) are commercially available.

Alternatively, the reducing agents of formula (VIII) or of formula (IX) can be prepared in situ starting from a solution of borane, complexed with THF or with $Me_2S$, by treatment with the corresponding amine of formula (VIIIa) or the corresponding pyridine of formula (IXa), wherein Y and W are as defined above.

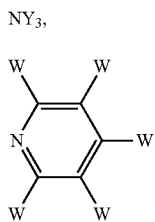

In a preferred aspect of the invention, the amine of formula (VIIIa) is a secondary amine, more preferably one Y is H and the remaining two of Y, taken together with the nitrogen atom to which they are bonded, form a morpholine, piperidine or piperazine ring. Preferably, the reducing agent of formula (VIII) is prepared in situ.

Further reducing agents suitable for the invention are borane complexed with THF or with $Me_2S$. These reducing agents are commercially available or can be prepared to turn in situ according to known methods.

Reducing agents of formula (VIII) or of formula (IX) result to be extremely efficient, economical, safe and hence advantageous in particular at an industrial level. Similarly, the isolation of the product from the reaction mixture and the disposal of wastewater results to be easier compared to other known double reductive amination procedures.

The reductive amination reaction can be optionally carried out in the presence of a solvent, selected for example from a dipolar aprotic solvent, typically dimethylformamide, dimethylacetamide, acetonitrile or dimethylsulphoxide; an ether, typically tetrahydrofuran or dioxane or methyl-tert-butyl ether; a chlorinated solvent, typically dichloromethane; an apolar solvent, typically toluene or hexane; an ester, such as ethyl acetate, isopropyl acetate or butyl acetate; a polar protic solvent, typically a $C_1$-$C_4$ alcohol, preferably methanol, or water, or a mixture of two or more, preferably two or three, of said solvents.

A salt of a compound of formula (V) or of formula (VII) is typically a pharmaceutically acceptable salt thereof.

The reductive amination can be carried out by treating the dicarbonyl compound of formula (VI) with at least stoichiometric amounts of an amine of formula (VII) and at least 2 moles of reducing agent of formula (VIII) or (IX) per mole of compound of formula (VI).

The reductive amination can be advantageously carried out at a reaction temperature between about −20° C. to about 40° C., preferably between about 0° C. to about 40° C., more preferably at about 25° C., and typically with a pH value of the reaction mixture between about 8 to about 4.

The pH value of the reaction mixture can be adjusted by adding acetic acid.

The double reductive amination step of a compound of formula (VI) may result in the formation of two diastereoisomers:

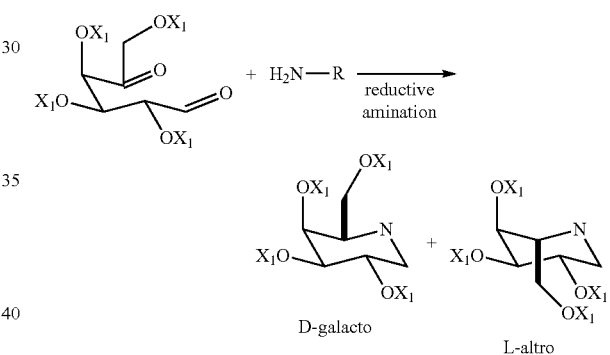

The formation of two diastereoisomers has been observed by Barili et al. (*Tetrahedron* 1997, 53, 3407). The authors performed the double reductive amination with the unprotected dicarbonyl (compound of formula (IVa)) and benzhydrylamine and found that solely the D-galacto isomer was formed with a yield of 36%. Performing the reductive amination with the diprotected dicarbonyl of formula (IVb) resulted in a mixture of 70:30 of D-galacto:L-altro diastereoisomers with a yield of 38%. Thus, performing the process starting from the diprotected compound of formula (IVb) provided the iminosugar in approximately the same yield as with the unprotected dicarbonyl of formula (IVa). In addition, the partial protection resulted in a mixture of two diastereoisomers, which were found to be inseparable by Thin Layer Chromatography (TLC) with several elution systems, even in the case of further protection of the free hydroxyls with an acetyl protecting group.

The inventors of the present invention have surprisingly found that the reaction of the tetraprotected benzyloxy compound of formula (VI) with $X_1$ being benzyl not only provided the iminosugar with significantly higher yields (68%), but also with a higher amount of the D-galacto isomer. In addition, both diastereoisomers could be separated by chromatography.

| Reference | Formed Product | Diastereomeric Ratio D-Galacto:L-Altro | Yield on Both Diastereoisomers |
|---|---|---|---|
| Barili | 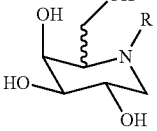 | 100:0 | 36% |
| Barili | 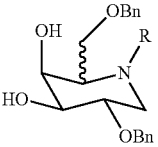 | 70:30 | 38%* |
| Present invention | 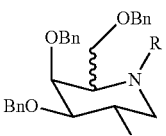 | 80:20 | 66% | with Bn = benzyl and R = benzhydryl
*the obtained product could only be purified and isolated as mixture of the two diastereoisomers after acetylation of the free hydroxyls. The yield refers to the bisacetylated compound.

The inventors of the present invention have also surprisingly found that the choice of the reducing agent and of the amine have an influence on the formation of the diastereoisomeric mixture.

For instance, the double reductive amination with benzylamine and NaCNBH$_3$ as reducing agent results in a diastereoisomeric mixture with a D-galacto: L-altro ratio of 2:1, whereas the use of borane morpholine, a reducing agent of the present invention of formula (VIII), leads to a diastereoisomeric ratio D-galacto:L-altro of 1:2.

The reaction of the tetrabenzyloxy compound of formula (VI) with (1S)-1-phenylethylamine and borane morpholine according to the invention provides a diastereomeric mixture D-galacto:L-altro of 24:76, whereas the process with (1R)-1-phenylethylamine and borane morpholine provides a diastereomeric mixture D-galacto:L-altro of 80:20.

After completion of the reaction, the mixture can be optionally washed with water, and the compound of formula (V) can be extracted with methods known to the person skilled in the art. For example, the compound of formula (V), optionally washed with water, extracted with an organic solvent, can be purified by crystallization or chromatography.

In a preferred embodiment, the mixture can be purified, including the separation of the D-galacto and/or L-altro isomer from a mixture thereof, by crystallization.

In a further preferred embodiment, the mixture can be purified, including the separation of the D-galacto and/or L-altro isomer from a mixture thereof, by chromatography.

The diastereomeric mixture can be purified for instance by normal-phase liquid chromatography (NPLC), for example by normal-phase flash column chromatography, using a solvent as eluent. The purification may be run in either isocratic or gradient elution modes.

A preferred eluent is chosen from dichloromethane, ethyl acetate, hexane or acetone, more preferable a mixture of hexane and ethyl acetate, for instance at a ratio of 9:1 (v:v).

Optionally, a compound of formula (V) can be converted into a pharmaceutically acceptable salt thereof according to known methods.

A further embodiment of the invention is a process as defined above for preparing the L-altro isomer of a compound of formula (V).

A further embodiment of the invention is a process as defined above for preparing the mixture of a compound of formula (V) and its L-altro isomer.

In case the alcohol-protecting group is allyl, such group can be removed according to known methods, for instance by isomerization followed by hydrolysis or by hydrogenation in the presence of Pd/C.

In case the alcohol-protecting group is acetyl or benzoyl, the removal can be obtained according to known methods, for instance by hydrolysis under acidic conditions or basic conditions.

In case the alcohol-protecting group is benzyl, such group can be removed by catalytic hydrogenation.

In case the amino-protecting group is benzyl, benzhydryl, phenylethyl, or benzyloxycarbonyl, the protecting group can be removed by catalytic hydrogenation.

In case the amino-protecting group is tert-butoxycabonyl, the protecting group can be removed by treatment with an acid, for example trifluoroacetic acid or hydrochloric acid.

A compound of formula (V), wherein R is an amino-protecting group, in particular benzyl, benzhydryl, triphenylmethyl, 1-phenylethyl or benzyloxycarbonyl, and each X is an alcohol-protecting group, in particular benzyl, can be converted into another compound of formula (V), wherein X and R are hydrogen, i.e. migalastat of formula (I) or a salt thereof, by removal of the protective groups according to known methods, for example, through catalytic hydrogenation.

A compound of formula (V), wherein R is hydrogen and each of X is an alcohol protecting group, in particular benzyl, can be converted into another compound of formula (V), wherein X and R are hydrogen, i.e. migalastat of formula (I) or a salt thereof, by removal of the protecting groups according to known methods, for example, by catalytic hydrogenation.

The catalytic hydrogenation can be carried out in the presence of homogeneous or heterogeneous metal catalysts, for example a catalyst based on Pd, Pt, Ni, Rh or Ru. Preferably, the catalyst is based on Pd.

In case of heterogeneous metal catalysts, the catalyst is preferably placed on an inert support, such as, for example, carbon, barium hydroxide, alumina, calcium carbonate; preferably charcoal. The concentration of the metal on the support may vary between about 1% and 30%, preferably between about 5% and 20%.

The employed hydrogen pressure may vary from about 1 atm to 40 atm, preferably from about 1 atm to 10 atm.

The molar quantity of the used catalyst, referred to a compound of formula (V), is comprised between about 0.1 and 10%, preferably between about 0.5 and 5%.

The reaction can be carried out in presence of an organic solvent chosen for example from a polar aprotic solvent, such as dimethylformamide, dimethylacetamide, acetonitrile or dimethylsulfoxide; an acyclic or cyclic ethereal solvent, typically tetrahydrofuran or methyl tert-butyl ether; a chlorinated solvent, typically dichloromethane; an apolar aprotic solvent, for example toluene or hexane; a polar protic solvent, for example a linear or branched $C_1$-$C_6$ alcohol, in particular methanol, ethanol, isopropanol or butanol; water; an ester, for example ethyl acetate, isopropyl acetate or butyl acetate; a linear or branched $C_3$-$C_7$ ketone, for example acetone, methyl ethyl ketone, or methyl isobutyl ketone; a carboxylic acid, for example acetic acid or propionic acid; or a mixture of two or more, typically two or three, of the above solvents.

Alternatively, the hydrogenation reactions can be carried out in a solution or a mixture of one, two or three organic solvents indicated above, comprising a mineral acid or base, for example hydrochloric acid or sulfuric acid, or sodium or potassium hydroxide.

Said hydrogenation reactions can be performed at a temperature between about 0° C. to the reflux temperature of the solvent or solvent-system benzyloxycarbonyl, preferably between about 25° C. and the reflux temperature. A further object of the present invention is a process for the preparation of migalastat of formula (I) or a pharmaceutical acceptable salt thereof, comprising the use of a compound of formula (V) obtained according to the process of the present invention.

According to a further aspect, the invention provides migalastat HCl in crystalline form, herein referred to as form I, characterized by an XRPD pattern having peaks at (expressed in ° in 2θ): 12.07; 13.58; 15.81; 16.37; 17.06; 17.53; 20.59; 21.59; 21.75; 22.67; 39.95; 24.92; 26.30; 27.16; 27.67; 28.37; 30.26; 30.81; 32.74; 33.11; 33.46, 33.87 and 34.52±0.2° in 2θ.

The preparation of a dicarbonyl compound of formula (VI)

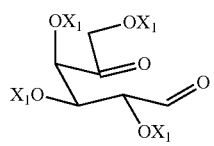

wherein each of the groups $X_1$, equal to each other, is an alcohol-protecting group, can be carried out by oxidation of a diol of formula (X),

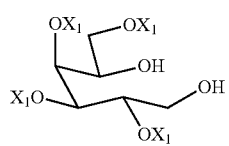

wherein each of $X_1$ is as defined above in the presence of an oxidizing agent and optionally a solvent.

The oxidation reaction may be carried out by methods known to the person skilled in the art, for example by the method making use of activated dimethyl sulfoxide (DMSO), reagents based on chromium ($CrO_3 \cdot Py_2$, PDC, PCC), oxidizing agents based on pentavalent iodine (Dess-Martin periodinane, IBX), TEMPO or NaOCl. Preferably, the oxidation reaction can be carried out with activated dimethyl sulfoxide (DMSO).

The oxidation reaction may be carried out by treating a compound of formula (X) with at least a stoichiometric amount of activated DMSO, for instance with about 2 moles of DMSO per mole of compound of formula (X).

DMSO can be activated by methods known to the person skilled in the art, for example using an activating agent, such as oxalyl chloride $(COCl)_2$, at a temperature ranging between −78° C. and −60° C., cyanuric chloride or trifluoroacetic anhydride at a temperature between −45° C. and −30° C., $Py_2 \cdot SO_3$ or $P_2O_5$ at a temperature between 0° C. and 30° C. The molar ratio between the activating agent and a compound of formula (X) is typically comprised between about 2:1 and 8:1, preferably between about 2:1 and 5:1. The reaction mixture is stirred for about 10 minutes to 2 hours, at a temperature suitable for activating the agents. Then, a base is added and the mixture is allowed to react for sufficient time for the completion of the oxidation, generally within less than 5 hours. The base may be an organic or inorganic base. Preferably, the base is an organic base, such as a tertiary amine, in particular triethylamine, diisopropylethylamine, diazabicycloundecene or diazabicyclooctane.

The oxidation reaction can be optionally carried out in the presence of a solvent, for example a dipolar aprotic solvent, typically dimethylformamide, dimethylacetamide, acetonitrile, DMSO; an ether, typically tetrahydrofuran, or dioxane or methyl tert-butyl ether; a chlorinated solvent, typically dichloromethane; an apolar solvent, typically toluene or hexane, an ester, for example ethyl acetate, isopropyl acetate or butyl acetate; a polar protic solvent, typically a $C_1$-$C_4$ alcohol, preferably methanol or water, or a mixture of two or more, preferably two or three, of said solvents; or using dimethylsulfoxide in an amount to be also the reaction solvent. Preferably, the solvent is DMSO.

A compound of formula (VI) can be isolated from the reaction mixture at the end of the reaction with methods known to the person skilled in the art. A compound of formula (VI), once extracted after washing with water, is preferably used as such in the subsequent reductive amination reaction to give a compound of formula (V), and then migalastat of formula (I) or a pharmaceutical acceptable salt thereof.

A further object of the present invention is a process for the preparation of migalastat of formula (I) or a pharmaceutical acceptable salt thereof, comprising the use of a compound of formula (V) or of formula (VI).

A compound of formula (X) can be prepared as reported for example in *Org. Lett.* 2007, 9, 879 by reducing a compound of formula (XI),

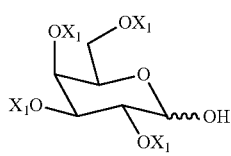

wherein each of $X_1$ is as defined above. The reducing agents and the optional solvents are known to the person skilled in the art.

A compound of formula (XI) is a derivative of D-galactose, which is commercially available or can be prepared starting from galactose by methods known to the person skilled in the art, for example as described in *Bull. Chem. Soc. Jpn.* 1976, 49(9), 2639.

The following examples further illustrate the invention.

Example 1: Synthesis of 2,3,4,6-tetra-O-benzyl-D-arabino-hexos-5-ulose of Formula (VI)

2.03 mL (23.8 mmol) of $(COCl)_2$ are dissolved under nitrogen atmosphere in 5 mL of $CH_2Cl_2$ and the solution is cooled down to −75° C. A solution of 2.12 mL (29.9 mmol) of DMSO in 5 mL $CH_2Cl_2$ is added dropwise over 15 minutes maintaining the temperature below −60° C., and the reaction mixture is stirred for further 35 minutes. A solution of 3.0 g (5.5 mmol) of 2,3,4,6-tetra-O-benzyl-D-galactitol of formula (X) (*Org. Lett.* 2007, 9, 879) in 10 mL of $CH_2Cl_2$ is then added to the mixture within 15 minutes maintaining the temperature below −60° C. and the reaction mixture is stirred for further 2 hours. 7.78 mL (55.9 mmol) of triethylamine (TEA) is then added dropwise over 20 minutes keeping the temperature below −45° C. Then, the solution of 2,3,4,6-tetra-O-benzyl-D-arabino-hexos-5-ulose of formula (VI) is allowed to reach room temperature and is used in the next step without further purification.

Example 2: Synthesis of (2R,3S,4R,5S)-2-[(phenylmethoxy)methyl]-3,4,5-tris-(phenylmethoxy)-piperidine of Formula (V)

The appropriate amine of formula (VII) (55.9 mmol), 5 mL (87.4 mmol) of acetic acid and 0.9 g (14.4 mmol) of $NaCNBH_3$ are dissolved at 0° C. in 20 mL methanol. The solution of 2,3,4,6-tetra-O-benzyl-D-arabino-hexos-5-ulose of formula (VI) as obtained as described in Example 1 is added to the above solution and the reaction mixture is stirred at 0° C. for 1.5 hours, then it is allowed to reach room temperature. The mixture is then cooled again down to 0° C. and 10 mL of $H_2O$ and 10 mL of 30% NaOH are slowly added. 30 mL of $CH_2Cl_2$ are added, the phases are separated and the aqueous phase is further extracted with $CH_2Cl_2$. The combined organic phases are washed with 20 mL of 3 M HCl, 30 mL of solution of 11% of NaOCl, 20 mL of a 10% solution of $Na_2S_2O_3$, 40 mL of a saturated solution of $NaHCO_3$ and $H_2O$ (2×25 mL). The organic phase is dried over anhydrous sodium sulfate, filtered and the solvent evaporated at reduced pressure. The crude reaction mixture is purified by flash chromatography (hexane/ethyl acetate 9:1, v:v) providing a mixture of 2 diastereomers (D-galacto and L-altro).

In the case of benzhydrylamine, the two diastereoisomers can be separated by flash chromatography (hexane/ethyl acetate 9:1, v:v)

| Amine of Formula (VII) | Diastereomeric Ratio D-galacto:L-altro | Yield on Both Diastereoisomers |
|---|---|---|
| $CH_3COONH_4$ | 82:18 | 46% |
| Butylamine | 83:17 | 57% |
| Benzhydrylamine | 80:20 | 66% |
| Benzylamine | 67:33 | 80% |

Example 3: Comparison of the Procedure of Barili et al. (*Tetrahedron* 1997, 53, 3407) with the Method of the Present Invention The authors of the present invention have applied the reaction conditions of Barili et al. (*Tetrahedron* 1997, 53, 3407), for compound of formula (VI) wherein $X_1$ is benzyl, using benzhydrylamine and $NaCNBH_3$ as reducing agent. Surprisingly, the product of formula (V) is obtained with a yield of 66%, which is much higher than the 36% reported for the unprotected dicarbonyl of formula (IVa) (with P=H). The reductive amination of 2,6-dibenzyl-dicarbonyl of formula (IVb) with P=Bn and subsequent acetylation step provides a mixture 70:30 of the 3,4-O-acetyl-N-benzhydrylamine D-galacto and L-altro derivative with a yield of 38%. The acetyl groups are then deprotected with sodium methoxide in methanol with a yield of 92%.

| | Diastereomeric Ratio D-Galacto:L-Altro | Yield on Both Diastereoisomers |
|---|---|---|
| Barili (IVa, P = H) | 100:0 | 36% |
| Barili (IVa, P = benzyl) | 70:30 | 38% |
| Present invention $X_1$ is benzyl | 80:20 | 66% |

Example 4: Synthesis of (2R,3S,4R,5S)-2-[(phenylmethoxy)methyl]-3,4,5-tris-(phenylmethoxy)-piperidines of Formula (V)

The appropriate amine of formula (VII) (55.9 mmol), acetic acid (5 mL, 87.4 mmol) and borane morpholine (1.45 g, 14.4 mmol) are dissolved at 0° C. in 20 mL of methanol. The solution of the compound of formula (VI) prepared as described in Example 1 is added to the mixture, which is stirred at 0° C. for 1.5 hours, then allowed to reach room temperature during the night. The mixture is then cooled down to 0° C. and $H_2O$ (10 mL) and 30% NaOH (10 mL) are added slowly. 30 mL of $CH_2Cl_2$ is added, the phases are separated and the aqueous phase is extracted with $CH_2Cl_2$. The organic phases are combined and washed with 3M HCl, 11% NaOCl solution, a 10% $Na_2S_2O_3$ solution, a saturated solution of $NaHCO_3$ and finally with water. The organic phase is dried over anhydrous sodium sulfate, filtered and the solvent evaporated at reduced pressure. The crude reaction mixture is purified by flash chromatography (hexane/ethyl acetate 9:1, v:v) resulting in a mixture of 2 diastereomers in absolute configuration respectively D-galacto and L-altro.

| Amine of formula (VII) | Diastereomeric ratio D-galacto:L-altro | Yield on 2 diastereoisomers |
|---|---|---|
| benzylamine | 33:67 | 78% |
| (1S)-1-phenylethylamine | 24:76 | 49% |
| (1R)-1-phenylethylamine | 80:20 | 68% |

Example 5: Synthesis of Migalastat of Formula (I)

1.95 g (2.83 mmol) of (2R,3S,4R,5S)-1-benzhydryl-2-[(phenylmethoxy)methyl]-3,4,5-tris-(phenylmethoxy)-piperidine of formula (V) are solubilized under nitrogen atmosphere in a mixture of 20 mL of MeOH and 1 mL of 6 M HCl. 300 mg of Pd/C 20% are added and the suspension is stirred under a hydrogen atmosphere at room temperature. At the end of the reaction, the suspension is filtered on a panel of perlite and concentrated. The obtained solid is stirred in MeOH, then filtered through a Buchner funnel and washed with methanol. After drying under vacuum at 50° C., 429 mg of the hydrochloride salt of migalastat in crystalline form, herein referred to as form I, and characterized by an XRPD pattern having peaks at (expressed in ° in 2θ): 12.07; 13.58; 15.81; 16.37; 17.06; 17.53; 20.59; 21.59; 21.75; 22.67; 39.95; 24.92; 26.30; 27.16; 27.67; 28.37; 30.26; 30.81; 32.74; 33.11; 33.46, 33.87 and 34.52±0.2° in 2θ, are obtained with a yield of 76% and a purity higher than 98%.

The invention claimed is:

1. A process for preparing a compound of formula (V), or a salt thereof,

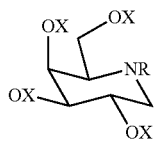

(V)

wherein each X, being the same, is hydrogen or an alcohol protecting group,

R is hydrogen, a $C_1$-$C_6$ alkyl, or an amino protecting group;

comprising carrying out a double reductive amination reaction of a compound of formula (VI),

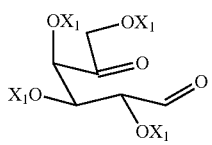

(VI)

wherein each $X_1$, being the same, is an alcohol protecting group, with an amine of formula (VII), or a salt thereof,

(VII)

NH$_2$—R wherein R is as defined above, in presence of a reducing agent and a solvent.

2. The process according to claim 1, wherein the alcohol-protecting group $X_1$ is benzyl, allyl, acetyl or benzoyl.

3. The process according to claim 1, wherein the alcohol-protecting group of $X_1$ is benzyl.

4. The process according to claim 1, wherein R is an amino protecting group chosen from benzyl, benzhydryl, triphenylmethyl, 1-phenylethyl, benzyloxycarbonyl or tert-butoxycarbonyl.

5. The process according to claim 1, wherein the reducing agent is NaCNBH$_3$, NaBH$_4$, NaBH(OAc)$_3$, or a borane complexed with an amine of formula (VIII) or with a pyridine of formula (IX)

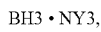

(VIII)

BH$_3$ · NY$_3$,

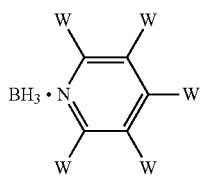

(IX)

wherein each of the substituents Y, which is the same or different, is hydrogen or an optionally substituted $C_1$-$C_6$ alkyl or aryl group, or two of Y, taken together with the nitrogen atom to which they are bound, form a $C_5$-$C_6$ heterocyclyl ring, which optionally contains an oxygen atom or a NRa group, wherein Ra is hydrogen, an amino protecting group or a $C_1$-$C_4$ alkyl group;

and each of the W substituents, which is the same or different, is hydrogen, an optionally substituted $C_1$-$C_6$ alkyl, or a halogen atom.

6. The process according to claim 1, wherein the reducing agent is a compound of formula (VIII), in which the corresponding amine of formula (VIIIa)

NY$_3$ (VIIIa)

is a secondary amine, in which one Y is H and the remaining two Y groups, taken together with the nitrogen atom to which they are bound, form a piperidine, morpholine or piperazine ring.

7. The process according to claim 1, wherein the reaction is carried out at a temperature between about −20° C. to about 40° C.

8. The process according to claim 1, wherein the compound of formula (V) or a salt thereof is further purified by crystallization or chromatography.

9. The process according to claim 1, wherein a compound of formula (VI)

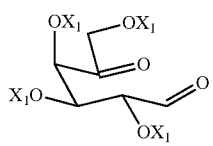

(VI)

is prepared by oxidizing a diol of formula (X),

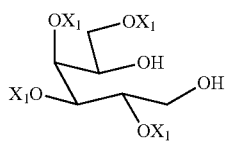

(X)

wherein each of the $X_1$ groups is as defined in claim 1, in presence of an oxidizing agent.

10. The process according to claim 9, wherein a compound of formula (X)

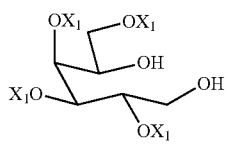

(X)

is prepared by reducing a compound of formula (XI),

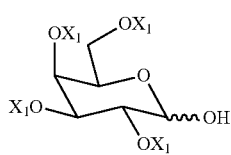

(XI)

wherein each of the $X_1$ groups is as defined in claim 1, in the presence of a reducing agent.

11. The process according to claim 1, further comprising the preparation of migalastat of formula (I), or a pharmaceutically acceptable salt thereof,

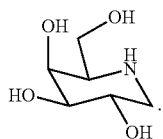

(I)

wherein each alcohol protecting group X and the amino protecting group R are removed by means of hydrogenation.

12. The process according to claim 11, comprising the removal of the protective groups in the compound of formula (V), wherein X is an alcohol protecting group and R an amino protecting group, to obtain a compound of formula (V), wherein X and R are hydrogen, and thus migalastat of formula (I).

13. A process for preparing a compound of formula (V)

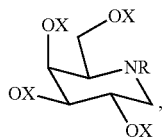

(V)

in a mixture with its L-altro diastereoisomer, wherein the mixture is enriched in the D-galacto diastereoisomer; and wherein the process comprises reacting a compound of Formula VI

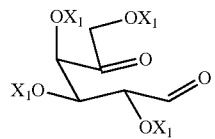

(VI)

with an amine of Formula (VII)

(VII)

wherein R is hydrogen, a $C_1$-$C_6$ alkyl, or an amino protecting group, in the presence of a borohydride reducing agent.

14. The process according to claim 11, wherein the compound migalastat HCl of formula (I) is in crystalline form I, characterized by an XRPD pattern having peaks at 12.1, 13.6, 15.8, 16.4, 17.1, 17.5, 20.6, 21.6, 21.8, 22.7, 23.9, 24.9, 26.3, 27.2, 27.7, 28.4, 30.3, 30.8, 32.7, 33.1, 33.5, 33.9, and 34.5±0.2° in 2θ.

15. The process according to claim 11, wherein the compound migalastat HCl of formula (I) is in crystalline form I, characterized by an XRPD pattern having peaks at 12.1, 13.6, 15.8, 16.4, 17.1, 17.5, 20.6, 21.6, 21.8, 22.7, 23.9, 24.9, 26.3, 27.2, 27.7, 28.4, 30.3, 30.8, 32.7, 33.1, 33.5, 33.9, and 34.5±0.2° in 2θ.

16. The process of claim 1, further comprising isolating and purifying the compound of Formula (V) by flash chromatography or by crystallization to remove the isomer 2S,3S,4R,5S and obtain purely the isomer 2R,3S,4R,5S.

* * * * *